United States Patent [19]

Mandrand et al.

[11] Patent Number: 6,017,707

[45] Date of Patent: *Jan. 25, 2000

[54] REAGENT AND METHOD FOR THE DETECTION OF A NUCLEOTIDE SEQUENCE WITH SIGNAL AMPLIFICATION

[75] Inventors: Bernard Mandrand, Villeurbanne; Philippe Cros; Thierry Delair, both of Lyons; Marie-Hélène Charles, Condrieu; Marie-Noëlle Erout, Sainte Foy les Lyon; Christian Pichot, Corbas, all of France

[73] Assignee: Bio Merieux, Marcy L'Etoile, France

[*] Notice: This patent is subject to a terminal disclaimer.

[21] Appl. No.: 08/870,730

[22] Filed: Jun. 6, 1997

Related U.S. Application Data

[62] Division of application No. 08/433,505, filed as application No. PCT/FR94/01084, Sep. 15, 1994, Pat. No. 5,695,936.

[30] Foreign Application Priority Data

Sep. 15, 1993 [FR] France ................................. 93 11006

[51] Int. Cl.[7] .............................. C12Q 1/68; C07H 21/02; C07H 21/04; C12N 15/00
[52] U.S. Cl. ............................ 435/6; 536/23.1; 536/24.3; 935/76; 935/77; 935/78
[58] Field of Search ................................. 435/6; 536/22.1, 536/23.1, 24.3; 935/77, 78

[56] References Cited

U.S. PATENT DOCUMENTS

| | | |
|---|---|---|
| 4,687,732 | 8/1987 | Ward et al. . |
| 4,731,325 | 3/1988 | Palva et al. . |
| 4,868,105 | 9/1989 | Urdea et al. . |
| 4,882,269 | 11/1989 | Schneider et al. . |
| 4,894,325 | 1/1990 | Englehardt et al. . |
| 4,925,785 | 5/1990 | Wang et al. . |
| 5,104,791 | 4/1992 | Abbott et al. . |
| 5,124,246 | 6/1992 | Urdea et al. . |
| 5,273,882 | 12/1993 | Snitman et al. . |
| 5,374,524 | 12/1994 | Miller . |
| 5,387,510 | 2/1995 | Wu . |
| 5,424,188 | 6/1995 | Schneider et al. . |
| 5,695,936 | 12/1997 | Mandrand et al. ........................ 435/6 |

FOREIGN PATENT DOCUMENTS

| | | |
|---|---|---|
| 0 153 873 | 9/1985 | European Pat. Off. . |
| 0 173 339 | 3/1986 | European Pat. Off. . |
| 0 204 510 | 12/1986 | European Pat. Off. . |
| 0 225 807 | 6/1987 | European Pat. Off. . |
| 88309697 | 10/1988 | European Pat. Off. . |
| 0 292 128 | 11/1988 | European Pat. Off. . |
| 0 317 077 | 5/1989 | European Pat. Off. . |
| 0 373 956 | 6/1990 | European Pat. Off. . |
| 91105249 | 4/1991 | European Pat. Off. . |
| 0 450 594 | 10/1991 | European Pat. Off. . |
| 2607607 | 6/1988 | France . |
| 88/02784 | 4/1988 | WIPO . |
| 89/03849 | 5/1989 | WIPO . |
| 90/00622 | 1/1990 | WIPO . |
| WO 91/08307 | 11/1990 | WIPO . |
| 91/08307 | 6/1991 | WIPO . |
| WO91/08307 | 6/1991 | WIPO . |
| 91/19812 | 12/1991 | WIPO . |

OTHER PUBLICATIONS

Nicholls et al., Journal of Clinical Laboratory Analysis 3 : 122–135 (1989).

The Stragene Catalog, p. 39 (1988).

Richard D. Abramson et al., "Nucleic Acid Amplification Technologies", *Current Opinion in Biotechnology*, pp. 41–47, May 14, 1993.

Konrad Misiura et al., "Biotinyl and Phosphotyrosinyl Phosphoramidite Derivatives Useful in the Incorporation of Multiple Reporter Groups on Synthetic Oligonucleotides", *Nucleic Acids Research*, vol. 18, No. 15, pp. 4345–4354, 1990.

Uwe Pieles et al., "A Protected Biotin Containing Deoxycytidine Building Block for Solid Phase Synthesis of Biotinylated Oligonucleotides", vol 18, No. 15, pp. 4355–4360, 1990.

Ricki Lewis, "PCR's Competitors are Alive and Well and Moving Rapidly Towards Commercialization", *Genetic Engineering News*, vol. 12, No. 9, pp. 1, 8–9, Jun. 1, 1992.

Sommer et al., Nucleic Acids Research 17(16) : p. 6749 (1989).

*Primary Examiner*—W. Gary Jones
*Assistant Examiner*—Ethan Whisenant
*Attorney, Agent, or Firm*—Oliff & Berridge, PLC

[57] ABSTRACT

Methods for the detection of a nucleotide sequence of interest comprising at least one nucleotide probe marked with a tracer. The methods include a reagent essentially comprising a linear backbone copolymer having lateral substituents, whose chain consists of a first type of repetitive unit and at least one other type of repetitive unit, in which at least one part of the units of the first type have a lateral substituent comprising a nucleotide unit, such a lateral substituent not being present on the other types of units. Each of said nucleotide units, all of which are identical, comprise at least one nucleotide sequence capable of hybridizing with said sequence of interest and nucleotide sequence capable of hybridizing with a probe, the reagent containing on average more than two of said nucleotide units, in molar equivalents, per mole of polymer. Such a reagent enables signal amplification to be obtained, and therefor lowers the sensitivity threshold. Application, in particular, in the production of tests for the detection of pathogenic organisms, or in the diagnosis of genetic diseases.

27 Claims, 3 Drawing Sheets

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:

(A) LENGTH: 37 bases
           (B) TYPE: nucleic acid
           (C) STRANDEDNESS: single
           (D) TOPOLOGY: linear (ii) MOLECULE TYPE: DNA (xi) SEQUENCE DESCRIPTION: SEQ ID NO:1:

TCATCCACCT GGCATTGGAC TGCCATAACC ATGAGTG                                    37

(2) INFORMATION FOR SEQ ID NO:2:

(i) SEQUENCE CHARACTERISTICS:
           (A) LENGTH: 22 bases
           (B) TYPE: nucleic acid
           (C) STRANDEDNESS: single
           (D) TOPOLOGY: linear (ii) MOLECULE TYPE: DNA (xi) SEQUENCE DESCRIPTION: SEQ ID NO:2:

TACTCACCAG TCACAGAAAA GC                                                    22

(2) INFORMATION FOR SEQ ID NO:3:

(i) SEQUENCE CHARACTERISTICS:
           (A) LENGTH: 22 bases
           (B) TYPE: nucleic acid
           (C) STRANDEDNESS: single
           (D) TOPOLOGY: linear (ii) MOLECULE TYPE: DNA (xi) SEQUENCE DESCRIPTION: SEQ ID NO:3:

GATGAGCTAT ATGAGAACGG TA                                                    22

(2) INFORMATION FOR SEQ ID NO:4:

(i) SEQUENCE CHARACTERISTICS:
           (A) LENGTH: 15 bases
           (B) TYPE: nucleic acid
           (C) STRANDEDNESS: single
           (D) TOPOLOGY: linear (ii) MOLECULE TYPE: DNA (xi) SEQUENCE DESCRIPTION: SEQ ID NO:4:

CCCCGAAGCG TTTTC                                                            15

(2) INFORMATION FOR SEQ ID NO:5:

(i) SEQUENCE CHARACTERISTICS:
           (A) LENGTH: 17 bases
           (B) TYPE: nucleic acid
           (C) STRANDEDNESS: single
           (D) TOPOLOGY: linear (ii) MOLECULE TYPE: DNA (xi) SEQUENCE DESCRIPTION: SEQ ID NO:5:

CGGTATGGTT TGCTGCT                                                          17

(2) INFORMATION FOR SEQ ID NO:6:

(i) SEQUENCE CHARACTERISTICS:
           (A) LENGTH: 20 bases
           (B) TYPE: nucleic acid
           (C) STRANDEDNESS: single
           (D) TOPOLOGY: linear (ii) MOLECULE TYPE: DNA (xi) SEQUENCE DESCRIPTION: SEQ ID NO:6:

GTCCAATGCC AGGTGGATGA                                                    20

(2) INFORMATION FOR SEQ ID NO:7:

(i) SEQUENCE CHARACTERISTICS:
             (A) LENGTH: 17 bases
             (B) TYPE: nucleic acid
             (C) STRANDEDNESS: single
             (D) TOPOLOGY: linear (ii) MOLECULE TYPE: DNA (xi) SEQUENCE DESCRIPTION: SEQ ID NO:7:

TACCGTTCTC ATATAGC                                                       17

(2) INFORMATION FOR SEQ ID NO:8:

(i) SEQUENCE CHARACTERISTICS:
             (A) LENGTH: 20 bases
             (B) TYPE: nucleic acid
             (C) STRANDEDNESS: single
             (D) TOPOLOGY: linear (ii) MOLECULE TYPE: DNA (xi) SEQUENCE DESCRIPTION: SEQ ID NO:8:

TCATCCACCT GGCATTGGAC                                                    20

(2) INFORMATION FOR SEQ ID NO:9:

(i) SEQUENCE CHARACTERISTICS:
             (A) LENGTH: 30 bases
             (B) TYPE: nucleic acid
             (C) STRANDEDNESS: single
             (D) TOPOLOGY: linear (ii) MOLECULE TYPE: DNA (xi) SEQUENCE DESCRIPTION: SEQ ID NO:9:

AAAAAAAAAA AAAAAAAAA AAAAAAAAA                                           30

(2) INFORMATION FOR SEQ ID NO:10:

(i) SEQUENCE CHARACTERISTICS:
             (A) LENGTH: 40 bases
             (B) TYPE: nucleic acid
             (C) STRANDEDNESS: single
             (D) TOPOLOGY: linear (ii) MOLECULE TYPE: DNA (xi) SEQUENCE DESCRIPTION: SEQ ID NO:10:

TTTTTTTTTT TTTTTTTTTT GTCCAATGCC AGGTGGATGA                              40

(2) INFORMATION FOR SEQ ID NO:11:

(i) SEQUENCE CHARACTERISTICS:
             (A) LENGTH: 29 bases
             (B) TYPE: nucleic acid
             (C) STRANDEDNESS: single
             (D) TOPOLOGY: linear (ii) MOLECULE TYPE: DNA (xi) SEQUENCE DESCRIPTION: SEQ ID NO:11:

CGCTTTTTTG CACAACATGG GGGATCATG 29

REAGENT AND METHOD FOR THE DETECTION OF A NUCLEOTIDE SEQUENCE WITH SIGNAL AMPLIFICATION

This is a Division of application Ser. No. 08/433,505 filed Jun. 14, 1995, which is the U.S. National Stage of PCT/FR 94/01084, filed on Sep. 15, 1994, now U.S. Pat. No. 5,695,936.

The present invention relates to a reagent and a method for detecting a nucleotide sequence in a sample.

It is often necessary, in techniques relating to nucleic acids and genetic material, to determine whether a gene, a part of a gene or a nucleotide sequence is present in a living organism, in a cellular extract from this organism or in a biological sample. Since any gene or part of a gene is, in theory, a specific sequence of nucleotide bases forming all or part of a nucleotide molecule, it is possible to look directly for the presence of a specific nucleotide sequence within a sample.

There is an immense interest in searching for specific nucleotide sequences in order to detect pathogenic organisms, to determine the presence of alleles, to detect the presence of lesions in a host genome and to detect the presence of a particular mRNA, or modification of a cellular host, to give some examples by way of illustration. Genetic diseases, such as Huntington's disease, Duchenne's myopathy, phenylketonuria and beta-thalassemia, can be diagnosed by means of analysing the DNA of the individuals concerned. Furthermore, diagnosis or identification of viruses, viroids, bacteria, fungi and parasite; can be achieved by means of hybridization experiments using nucleic acid probes.

Different types of methods for detecting nucleic acids are described in the literature. These methods are based on the purine-pyrimidine pairing properties of the nucleic acid complementary strands in the DNA-DNA, DNA-RNA and RNA-RNA duplexes. This process of pairing is achieved by the establishment of hydrogen bonds between the adenine-thymine (A-T) bases and the guanine-cystosine (G-C) bases of the double-stranded DNA. Adenine-uracil (A-U) base pairs can also be formed by means of hydrogen bonds in the DNA-RNA or RNA-RNA duplexes. The pairing of the nucleic acid strands in order to determine the presence or the absence of a given nucleic acid molecule is commonly termed "nucleic acid hybridization" or simply "hybridization".

Based on the properties of the nucleic acids, techniques have been developed which make it possible to detect, and to quantify, a nucleic acid, termed the target, in a sample under analysis. These techniques can be divided into two broad categories: techniques termed direct detection techniques, such as those developed by Southern, E. M. (J. Mol. Biol., 98, 503, (1975)) and the technique termed "dot-blot" (Maniatis et al., Molecular Cloning, Cold Spring Harbor, (1982)) for detecting DNA, or the Northern technique for detecting RNA, and the techniques termed indirect techniques, such as the sandwich or "reverse dot" technique (see, for example, Dunn A. R. and Hassel J. A, Cell, 12, 23 (1977)); Ranki M. et al., Gene, 21, 77 (1983); Palva A. et al., FEMS Microbiol. Lett. 23, 83 (1984); Polskycynki R. et al., Clin. Chem., 31, 1438 (1985); Saiki R. K. et al., Proc. Natl. Acad. Sci. U.S.A., vol 86, 6230–6234 (1989)).

One of the principal difficulties encountered when developing a test for detecting a target nucleotide sequence of interest is the threshold of sensitivity of the hybridization methods. As a consequence, various methods have been described which have the purpose of increasing the detecting power of these hybridization techniques. These methods, termed "amplification methods", can take place at different stages in a detection process which uses nucleic acid probes. These stages can be classified in two categories: amplification of the target or amplification of the signal. The articles by Lewis (1992. Genetic Engineering News, 12, 1–9) on the one hand, and by Abramson and Myers (1993. Curr. Opin. Biotechnol., 4, 41–47), on the other, represent good general reviews of target amplification.

The major disadvantage of these techniques resides in the difficulty of quantifying the nucleic acid target of interest following the amplification step.

Other approaches relating to signal amplification have been described.

Palva A. M. et al., in U.S. Pat. No. 4,731,325, and Urdea M. S. et al., in European Patent 0 225 807, increase the number of detection probes which are able to hybridize with the target. In many cases (necessity of differentiating closely related species in bacteriology or detecting genetic diseases), it is not possible to employ this technique since only one specific sequence in the target can be used for hybridizing to a detection probe.

A certain number of techniques which have been described consist in increasing the number of tracers, i.e. molecules which are able to generate a signal, directly or indirectly, on the detection probe. The tracer can, in particular, be a biotin, a fluorophore, an enzyme or a radioactive group. The detection probe is attached to a polymer, which can be a nucleotide, to which a number of tracers greater than two are attached, most frequently covalently (see Ward D. C. et al. U.S. Pat. No. 4,687,732, Bahl C. et al. EP 0 373 956, Ylikoski J. et al. WO 88/02784, Kwiatkowski M. et al. WO 90/00622, Segev D. et al. EP 0 292 128, Haralambidis J. et al. WO 89/03849, Rabbani E. et al. EP 0 173 339).

One of the disadvantages of these techniques resides in the need to carry out a controlled coupling between the probe and the number of tracers employed. This double coupling is not easy to control in order to obtain a maximum number of tracers on a detection probe. Systems in which the tracer is incorporated in a controlled manner, for example during the automated synthesis of oligodeoxyribonucleotides, have been described (Pieles U. et al., Nucleic Acids Research, 18, 4355–4360 (1990) or Misiura K. et al., Nucleic Acids Research, 18, 4345–4354 (1990)). However, in this case, the number of tracers incorporated is low due to the limitations of synthesizing on a solid support. Furthermore, when the number of tracers increases, the detection probe is easily masked by the tracers, and the efficiency of hybridization with the target declines.

These same disadvantages are met with in the system described by Schneider R. J. et al. in U.S. Pat. No. 4,882, 269. A probe, termed the primary probe, which is nucleotide in nature and which has a ail consisting of some type of polymer, hybridizes to the target. This tail can carry a tracer which can be detected by a suitable secondary probe. When the tail is nucleotide in nature, the secondary probe is a nucleotide and can hybridize with the tail. For the system to function, a nucleotide tail is required which is a large size and which has a different sequence from that of the primary probe, and it is necessary to increase the number of labelled secondary probes. In practice, this is achieved by molecular biological techniques with the primary probe being cloned into a phage such as M13 and the secondary probes being complementary to different sequences of the phage.

Another closely related system is described by Chiswell D. J. in European Patent 0 153 873. Chiswell presents an assay in which part of a nucleic acid probe, termed the primary probe, hybridizes with the target. This primary probe includes a seconds part to which a second, multilabelled, probe, termed the secondary probe, can hybridize. For implementation in practice, these primary probes are made by molecular biological techniques, such as cloning (for example cloning a specific sequence of the target in an M13 fragment), which are ill-suited to manufacturing procedures on a large scale.

Collins M. L. (EP 0 204 510) describes a method in which the nucleic acid target is brought into contact with a first probe, called the receptor probe, a second probe, called the amplifying probe, and a third probe, which is called the labelled probe and which is able to hybridize with the second, amplifying, probe. The receptor probe, which hybridizes with the target, possesses a homopolymeric nucleotide tail (for example polyA). The amplifying probe contains a sequence which is complementary to the tail (for example polyT). The labelled probe contains a nucleotide sequence which is able to hybridize with the amplifying probe (for example labelled polyA). This combination of probes constitutes a stacking, leading to signal amplification.

Another type of stacking is also described by Segev D. in European Patent 0 450 594.

In these two cases, the stackings which are produced in the hybridization medium are not controlled and lead to poor reproducibility, and therefore to quantification problems. Furthermore, increasing the number of successive hybridization steps generates losses which result in only a modest gain being achieved in signal amplification.

A reagent has now been found for the detection, including the quantitative detection (measurement), of a nucleotide sequence of interest in a sample which is likely to contain it, which reagent eliminates the abovementioned disadvantages and makes it possible to control signal amplification efficiently and quantitatively.

The invention relates to a kit for detecting a sequence of a nucleotide sequence of interest, with signal amplification, which kit comprises at least one nucleotide probe which is labelled with a tracer, characterized in that it contains, in suitable containers, a reagent essentially comprising a linear backbone copolymer carrying lateral substituents, whose chain consists of a first type of repetitive unit and of at least one other type of repetitive unit, in which at least a part of the units of the first type carry a lateral substituent comprising a nucleotide unit, such a lateral substituent not being present on the other types of unit, each of the said nucleotide units, all of which are identical, comprising, at least, a nucleotide sequence which is capable of hybridizing with the said sequence of interest and a nucleotide sequence which is capable of hybridizing with the said probe, the said reagent containing on average more than two of the said nucleotide units, in molar equivalents, per mole of polymer.

The sequence of interest is, in particular, a single-stranded nucleotide sequence which may, if appropriate, be obtained by prior denaturation of a hybrid (DNA-DNA, DNA-RNA or RNA-RNA) using standard techniques (physical, chemical or enzymic). The signal amplification system of the invention can also be employed to detect a double-stranded sequence by implementing the triple helix technique, to which it can be applied.

The copolymer of the reagent of the invention has a linear backbone which is essentially carbonaceous. That is to say, the polymer chain is formed essentially by a sequence of carbon-carbon covalent bonds. The nucleotide units are present in the form of lateral substituents which are bonded to the polymeric backbone, directly or indirectly, by covalent bonds. The polymeric backbone can, where appropriate, carry other lateral substituents which are present on a starting monomer, including lateral substituents which are capable of being involved in the bond with the nucleotide unit but which have not reacted with the precursor of the latter. The copolymer is, in particular, a bipolymer.

The units of the copolymer which are not involved in the establishment of a bond with the nucleotide unit serve, in particular, to space out, in the copolymer, the units which carry the nucleotide units, and can also serve to modulate, in a known fashion, the properties of the copolymer, for example the solubility properties.

According to a first embodiment, the reagent which is used in accordance with the invention is characterized in that, in one and the same nucleotide unit, the said sequences which are capable of hybridization are distinct and non-overlapping, and in that the said nucleotide sequence capable of hybridization with the probe is in that case a sequence which is chosen arbitrarily.

In a system which uses such a reagent, the labelled probe can be employed as a universal detection probe. Moreover, such a system is well suited, more specifically, for effecting detection in one step, in particular without intermediate wash(es).

In another embodiment, the reagent which is used in accordance with the invention is characterized in that, in one and the same nucleotide unit, one of the said sequences capable of hybridization is included in the other. That is to say, one of the said sequences consists of a part of the other sequence, or else, in the limit, the two sequences are mixed together (they are identical) and, in fact, only form one sequence, in the nucleotide unit. In this embodiment, the labelled probe must, of course, be suitable for the target (sequence of interest): either the probe is identical with the sequence of interest, or else the probe must at least be able to hybridize with the sequence which is complementary to the sequence of interest.

In general, a molecule of the reagent which is used in accordance with the invention contains on average from 3 to 100 and, in particular, from 5 to 50, nucleotide units such as defined above.

The reagent which is used in accordance with the invention can be considered (independently of the actual method by which it is obtained) as a conjugate in which the nucleotide units are coupled to a base copolymer. For this reason, this reagent is sometimes referred to, in that which follows, as a "detection conjugate".

While the copolymer underlying the reagent according to the invention is not necessarily soluble in aqueous media (always employed in practice in techniques for detecting nucleic acid targets), the detection conjugate must be.

This copolymer is preferably a copolymer which has a molecular weight of between 5000 and 400,000, for example between 10,000 and 150,000.

The nucleotide units which are present in the amplification reagent of the invention are generally oligonucleotides which have a length of from 5 to 100 nucleotides and, preferably, of from 10 to 40. In general, the reagent of the invention contains, in molar equivalents, from 3 to 100 nucleotide units per mole of copolymer, preferably from 5 to 50, for example from 10 to 30.

According to the specific embodiments of the invention, taken in isolation or, where appropriate, in combination:
the copolymer is a bipolymer;
the said copolymer has a linear backbone which is essentially carbonaceous;

the said repetitive units result from the copolymerization of a first unsaturated monomer with at least one other unsaturated monomer;

the said first unsaturated monomer carries a reactive function which is able to react (with the establishment of a covalent bond), either directly or using a bifunctional coupling reagent as intermediate, with a precursor of the said nucleotide unit in order to form the said lateral substituent; the reactive function can be protected, in a known manner, during the copolymerization, and then deprotected for the reaction with the precursor;

the said reactive function is selected from among the amide, imide, aldehyde, epoxy, thiol, halogenoalkyl or carboxylic acid functions, with the carboxylic acid being, where appropriate, activated in acid halide form, in anhydride form or in ester form.

the said first monomer is a derivative of an unsaturated carboxylic acid; in particular acrylic acid, methacrylic acid or maleic acid; the derivative is an anhydride, an acid halide or an ester;

the said second monomer is selected from among N-vinylpyrrolidone, methyl vinyl ether, ethylene, propylene and styrene.

The coupling of nucleotide units to a copolymer can be carried out using methods which are termed direct or indirect and which are well known.

For example, in the case of a direct method, an oligonucleotide derivative (precursor of the nucleotide unit) is synthesized which has a reactive function at any site in the nucleotide chain, for example at the 5' end or at the 3' end, or on a nucleotide base or on an internucleotide phosphate, or else on the 2' position of the nucleotide sugar. The oligonucleotide derivative is then coupled to a copolymer which has previously been prepared and which includes a reactive function which is complementary to that of the oligonucleotide derivative, that is, such that the reaction of the two reactive functions with each other permits establishment of a covalent bond between the oligonucleotide and the copolymer. As examples of reactive function couples, it is possible to couple primary amines with an activated carboxylic acid (for example in anhydride form or in the form of an ester of N-hydroxysuccinimide), or an aldehyde, or else a thiol function with a halogenoalkyl function.

In the method of indirect coupling, the polynucleotide and the copolymer each carry a reactive function, it being possible for these reactive functions to be identical or to be different from each other; these two functions are not complementary, but are capable of reacting with an intermediate coupling agent which is a bifunctional reagent (homobifunctional if the two functions are identical or heterobifunctional if the two functions are different). Among those homobifunctional coupling agents which may be cited are DITC (1,4-phenylene diisothiocyanate), DSS (disuccinimidyl suberate) or the like when the two reactive functions are primary amine functions. Among those heterobifunctional coupling agents which may be cited are SMCC (succinimidyl-4-(N-maleimidomethyl)cyclohexane-1-carboxylate), when the two reactive functions display, each independently of the other, a primary amine function and a thiol function, SMPB (succinimidyl-4-(p-maleimidophenyl)butyrate) or the like.

After the oligonucleotide has been coupled to the copolymer, any excess of reactive functions in the copolymer is neutralized in a manner which is known per se. For example, the aldehyde groups which are in excess can be neutralized with a primary amine such as ethanolamine, and the maleimide groups can be neutralized with a thiol (such as thioethanolamine or dithiothreitol), etc.

Use is made, in particular, of copolymers which are based on N-vinylpyrrolidone (abbreviation NVP) or maleic anhydride.

The copolymer based on NVP, preferably a bipolymer, results from the copolymerization of a monomer of N-vinylpyrrolidone and a second monomer which is an unsaturated compound which can be copolymerized with NVP. The second monomer is, in particular, the carrier of a reactive function which enables a covalent coupling to be established between the oligonucleotide units and the copolymer. For example, the second monomer can carry a reactive function such as aldehyde, epoxy, halogenoalkyl, primary amine, thiol, maleimide or ester (preferably an ester function of N-hydroxysuccinimide) or a function which can be activated such as a carboxyl function (which can be activated, in particular, by formation of an hydroxysuccinimide ester) or such as a hydroxyl function (which can be activated, in particular, by cyanogen bromide). In particular, the two monomers are N-vinylpyrrolidone and N-acryloxysuccinimide (copolymers are obtained which are termed NVPNAS). From 25 to 70% of the units of the copolymer consist, in particular, of units derived from N-vinylpyrrolidone, with the other units deriving from acrylic acid.

The copolymer based on maleic anhydride, preferably a bipolymer, results from the copolymerization of a maleic anhydride monomer and at least a second monomer, in particular an unsaturated monomer, which can be copolymerized with the maleic anhydride. The second monomer is suitable for ensuring efficient behaviour of the oligonucleotide-copolymer conjugate in solution, with this second monomer not displaying any function which is capable of reacting with an oligonucleotide unit. The covalent coupling between the oligonucleotide unit and the copolymer is effected with the aid of anhydride groups (originating from the starting monomer), by reaction with a derivative of the oligonucleotide precursor of the said oligonucleotide unit or by the mediation of a coupling agent. The second monomer can be ethylene, styrene, propylene or methyl vinyl ether. In particular, the two monomers are maleic anhydride and methyl vinyl ether, and the corresponding copolymers are termed AMVE. From 35 to 65%, in particular between 45 and 55%, of the units in the copolymer consist, especially, of units derived from maleic anhydride.

The maleic anhydride/methyl vinyl ether (AMVE) and N-vinylpyrrolidone/N-acryloxysuccinimide (NVPNAS) copolymers are, in particular, linear copolymers which can, in general, be obtained in the form of copolymers of the alternating type.

The invention also relates to the use of a reagent, which consists of the detection conjugate as defined above, as a signal amplification reagent in a method for detecting a nucleotide sequence of interest.

The sequence of interest is either a sequence of the target substance (that which it is in fact desired to detect) or a sequence which is linked to the target substance, or else, in competition methods, a sequence which is linked to an analogue of the target substance which is a competitor of the latter.

The invention relates, in particular, to a method for detecting, with signal amplification, a nucleotide sequence of interest which is capable of being immobilized on a solid support, in which method a nucleotide detection probe is used which is labelled with a tracer, characterized in that:

a reagent as defined above,
and the labelled detection probe,
are added to a liquid medium which is in contact with the said solid support, under conditions permitting hybridization, and the possible presence of the tracer, immobilized on the solid support, is then demonstrated using customary methods.

The method of the invention can be applied, in particular, for detecting and/or measuring the amount of a target nucleic acid fragment which may be present in a sample. The nucleotide sequence of interest is a specific part of the nucleotide sequence of the target, which part can be selected, in particular, as the means for characterizing a species, a genus, an allele or the like. The nucleotide sequence of interest is fixed onto the solid support either directly or indirectly with the mediation of a ligand. The ligand can, in particular, be a capturing probe which is selected for being complementary to another region of the target, in accordance with the sandwich technique, which is well known. In another embodiment of the sandwich technique, the capturing probe is itself attached to a copolymer in order to be fixed onto the solid support by passive adsorption, that is, without the formation of a covalent bond between the support and the copolymer which carries the capturing probe. This method can contribute to a reduction in the background noise. By means of simple, routine experiments, it is possible to select the copolymer(s) (identical or different) which ensure(s) satisfactory attachment of the capturing probe, by passive adsorption, to the support, and a signal amplification which is accompanied by a reduction in the background noise, resulting in an increase in sensitivity. The sequence of interest can also be attached directly to the solid support by way of the target, in accordance with the "reverse dot" technique.

The method of the invention is also applicable to immunoassays, and, in particular, to the detection of haptens, antigens, polypeptides or antibodies in procedures which do or do not involve competition. For example, the sequence of interest can be attached, preferably by covalent bonding, to a ligand which is capable of reacting specifically with a target molecule. In competition techniques, the sequence of interest can be attached, preferably covalently, to a ligand, the said ligand being capable of competing with the target for attachment to a specific anti-ligand. The techniques for coupling a ligand to the sequence of interest depend on the nature of the ligand and are well known. It is, of course, necessary to select a coupling method which does not alter the ability of the ligand to recognize the anti-ligand, something which can readily be verified by simple routine experiments.

As an illustration, if the target to be measured is an antigen, the sequence of interest is attached to an antibody which is specific for the antigen. After having reacted with the antigen, this antibody can react, by way of the sequence of interest, with the oligonucleotide-copolymer reagent of the invention. A detection probe which is complementary to at least part of the sequence of interest, attached to the copolymer, renders it possible to detect the antigen with satisfactory sensitivity.

If the oligonucleotide unit of the reagent comprises a sequence which is specific for the sequence of interest and an arbitrary sequence, the detection probe will be complementary to the arbitrary sequence. It is possible to reduce the number of steps by using a suitable buffer which permits both reaction of the ligand with the anti-ligand and hybridization of the nucleotide sequences to each other. It is possible to achieve a one-step assay, with the antibody attached to the sequence of interest, the copolymer-oligonucleotide detection reagent and the detection probe reacting during the same incubation.

Similarly, a second oligonucleotide-copolymer conjugate can be used as the capturing conjugate in a sandwich immunoassay in combination with the detection conjugate, on condition that the capturing anti-ligand is coupled to a nucleotide sequence which is complementary, at least in part, to the sequence which is attached to the capturing conjugate. A reduction in the background noise, combined with an increase in the signal, leads, by means of selecting suitable conjugates, to an increase in sensitivity.

The copolymers which are used in accordance with the invention are preferably bipolymers. They can be obtained, in a manner known per se, by the free radical route, by the ionic route, by polycondensation reaction, or by group-transfer reaction. Preferably, they are copolymers which are obtained by free radical copolymerization of ethylenically unsaturated comonomers, one of which possesses a reactive function which is suitable for covalently attaching the lateral nucleotide substituents.

The term "solid support", as employed here, includes all materials on which it is possible to immobilize an oligonucleotide for use in diagnostic tests, in affinity chromatography and in separation procedures. Natural or synthesized materials, which have or have not been modified chemically, can be used as the solid support, in particular polysaccharides such as cellulose-based materials, for example paper, cellulose derivatives such as cellulose acetate and nitrocellulose, dextran; polymers such as vinyl polychlorides, polyethylenes, polystyrenes, polyacrylates, polyamides, or copolymers based on aromatic vinyl monomers, alkyl esters of alpha-beta unsaturated acids, esters of unsaturated carboxylic acids, vinylidene chloride, dienes or compounds exhibiting nitrile functions (acrylonitrile); polymers of vinyl chloride and propylene; polymers of vinyl chloride and vinyl acetate; copolymers based on styrenes or substituted derivatives of styrene; natural fibres such as cotton and synthetic fibres such as nylon; inorganic materials such as silica, glass, ceramic and quartz; latexes, that is, an aqueous colloid dispersion of any polymer insoluble in water; magnetic particles; metallic derivatives. The choice of a support material can be made, in each particular case, on the basis of simple routine experiments.

Preferably, the solid support which is used in the present invention is a polystyrene polymer, a butadiene-styrene copolymer, or a butadiene-styrene copolymer which is mixed with one or more polymers or copolymers selected from among polystyrene, styrene-acrylonitrile or styrene-methyl methylmethacrylate copolymers, polypropylenes, polycarbonates or the like. The solid support which is used is, in particular, a polystyrene or a styrene-based copolymer which contains between about 10 and 90% by weight of styrene units.

The solid support according to the invention can be, in the forms which are customarily suitable, for example, in the form of a microtitration plate, a sheet, a cone, a tube, a well, beads, particles or the like.

The term "oligonucleotide unit", as employed in the present application, refers to a linking-together of at least 5 deoxyribonucleotides or ribonucleotides, where appropriate including at least one modified nucleotide, for example at least one nucleotide having a modified base such as inosine, methyl-5-deoxycytidine, dimethylamino-5-deoxyuridine, deoxyuridine, diamino-2,6-purine, bromo-5-deoxyuridine or any other modified base which permits hybridization.

This polynucleotide can also be modified at the level of the internucleotide bond, as for example in the case of phosphorothioates, H-phosphonates and alkyl phosphonates, or at the level of the backbone, as for example in the case of alpha-oligonucleotides FR 2 607 507) or PNAs (M. Egholm et al., J. Am. Chem. Soc., (1992), 114, 1895–1897). These various modifications can, where appropriate, be taken in combination.

The tracers which are employed to label the detection probe are selected from among the customary tracers. These are, for example:

- enzymes which produce a signal which can be detected, for example, by colorimetry, fluorescence or luminescence, such as horseradish peroxidase, alkaline phosphatase, beta galactosidase and glucose-6-phosphate dehydrogenase;
- chromophores, such as fluorescent and luminescent compounds and dyes;
- electron dense groups detectable by electron microscopy or by their electrical property such as conductivity, amperometry, voltametry or impedance measurements;
- groups detectable by optical methods (such as diffraction, surface plasmon resonance, or variation in contact angle) or by physical methods such as atomic force spectroscopy or tunnel effect;
- radioactive molecules such as $^{32}P$, $^{35}S$ or $^{125}I$.

The covalent or non-covalent methods used for attaching these tracers depend on the tracers and are well known by the person skilled in the art.

Indirect systems can also be used, for example those which include haptens which can be detected by a specific antibody, or a protein, such as the biotin/avidin or streptavidin couple, or else a sugar/lectin couple. In this case, it is the antibody or the protein which carries a tracer.

Nucleic acid hybrids of the DNA/DNA, RNA/RNA and DNA/RNA type can be detected by anti-hybrid antibodies or by specific proteins such as phage polymerases.

If the detection probe consists of modified nucleotides such as alpha-anomeric nucleotides or PNAs (P. E. NIELSEN et al, Science, 254, 1497–1500 (1991)), anti-alpha-nucleotide or anti-PNA antibodies can be employed.

The term "antibody" refers, in particular, to monoclonal or polyclonal antibodies, antibody fragments and antibodies obtained by genetic recombination.

The term "hapten" refers to a molecule which, while being of insufficient size to be immunogenic, can be used to obtain antibodies which recognize it, by immunizing animals after it has been coupled to a protein, for example.

A sequence which is homologous to another sequence refers to a sequence which is able to hybridize with a sequence which is strictly complementary to the said other sequence.

Passive fixation is understood to mean a fixation which is due to forces other than the forces of covalent bonding.

BRIEF DESCRIPTION OF THE DRAWINGS

In the attached drawings, where the same letters or reference numbers always refer to the same element.

1 represents a solid support.
2 represents the capturing probe which is fixed to the solid support by some appropriate means.
3 represents the target nucleic acid to be detected.
D represents the detection probe and T represents the tracer.

Figure 1:
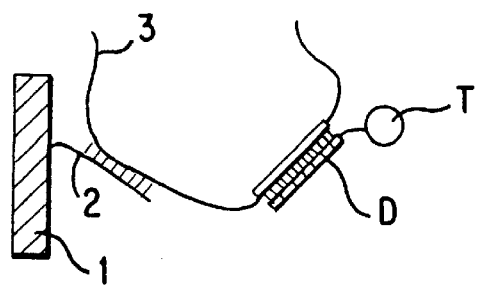
FIG. 1 diagrammatically depicts the direct sandwich protocol according to the conventional methods for detecting a nucleic acid.
Figure 2:
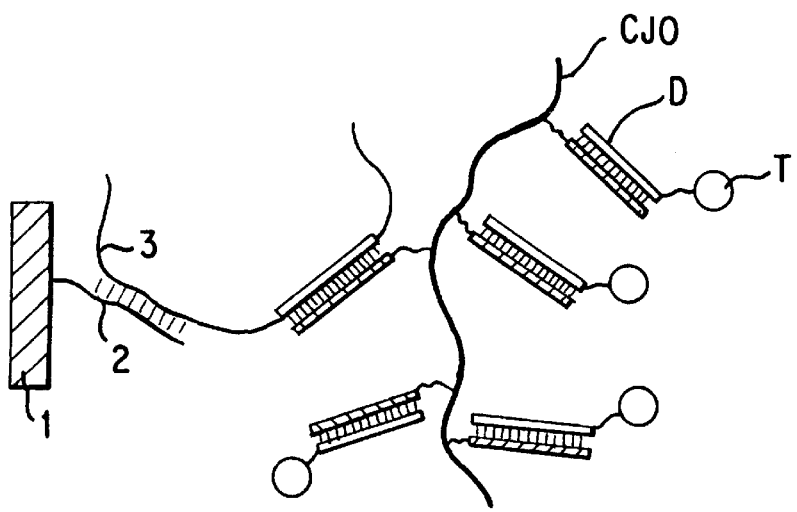

FIG. 2 depicts a sandwich protocol in which a detection conjugate reagent of the invention is used to amplify the signal.

1 represents the solid support.
2 represents the capturing probe which is fixed to the solid support by some appropriate means.
3 represents the target nucleic acid to be detected.
D represents the detection probe and T represents the tracer.
CJO represents the copolymer-oligonucleotide conjugate. The oligonucleotide unit (represented by a black rectangle), which is attached to the copolymer, is complementary to part of the target which is termed the sequence of interest (represented by a white rectangle). The detection probe D is homologous to the target.

Figure 3:
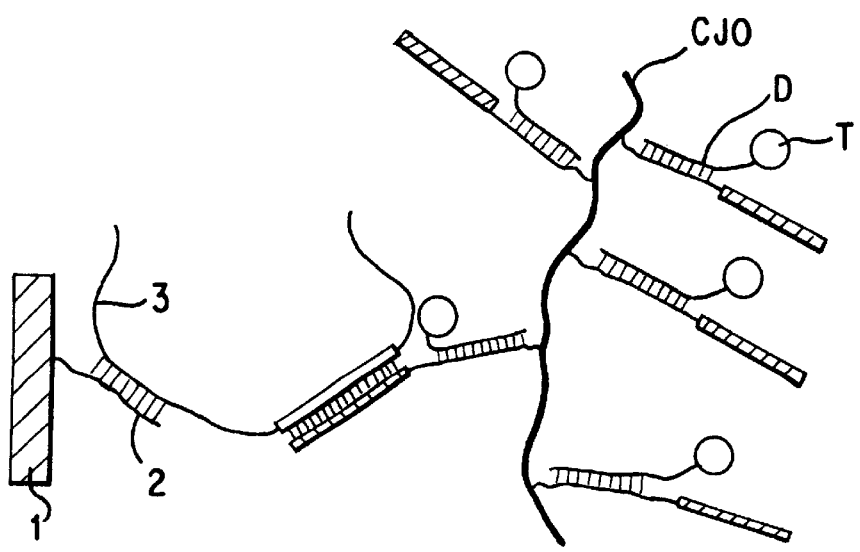

FIG. 3 depicts a sandwich protocol using a detection conjugate to amplify the signal. In this case, there cannot be any competition between the target and D.

1 represents the solid support.
2 represents the capturing probe which is fixed to the solid support by some appropriate means.
3 represents the nucleic acid target to be detected.
D represents the detection probe and T represents the tracer.
CJO represents the copolymer-oligonucleotide conjugate. The nucleotide unit which is attached to the copolymer consists of two parts. One of the parts (represented by a black rectangle) is complementary to the sequence of interest (represented by a white rectangle). The other part, represented by an unthickened line, has an arbitrary sequence. The detection probe D is complementary to this arbitrary sequence.

Figure 4:
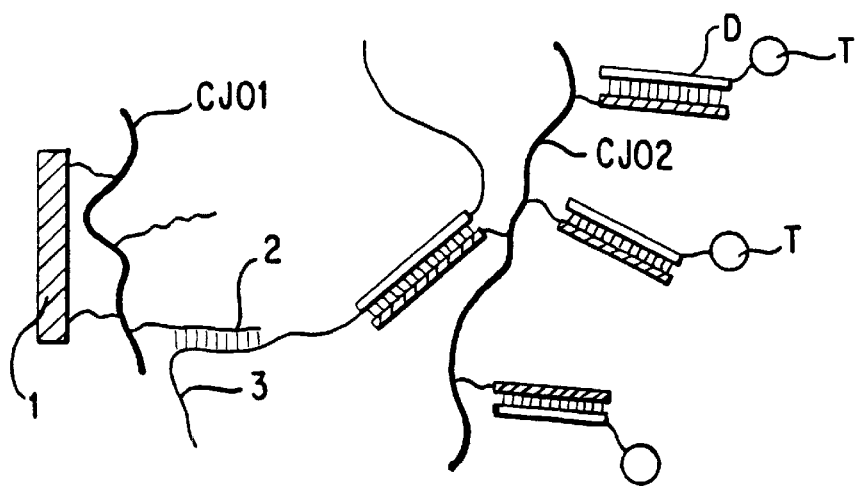

FIG. 4 depicts a sandwich protocol which uses a detection conjugate and a capturing conjugate.

1 represents the solid support.
2 represents the capturing probes, which is fixed to the solid support by way of a capturing conjugate CJO1. The capturing probe is covalently attached to the copolymer in order to form CJO1, which is fixed by passive adsorption to the support.
3 represents the nucleic acid target to be detected.
D represents the detection probe and T represents the tracer.
CJO2 represents the copolymer-oligonucleotide conjugate. The oligonucleotide unit (represented by a black rectangle), which is attached to the copolymer, is complementary to the sequence of interest (represented by a white rectangle). The detection probe D is homologous to the sequence of interest. As in FIG. 3, an oligonucleotide unit can be used which includes an arbitrary sequence. D is then complementary to this arbitrary sequence.

The two copolymers making up CJO1 and CJO2 can be identical or different, but the two polynucleotides which are respectively attached to these copolymers are complementary to two distinct regions of the target to be detected.

Figure 5:
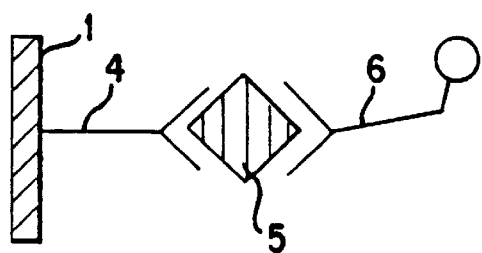

FIG. 5 depicts a direct sandwich immunological protocol in accordance with the conventional methods for antigen detection.

1 represents the solid support.
4 represents a first, capturing, antibody, which is fixed to the support by some suitable means.

5 represents an antigen.

6 represents a second, detection, antibody, which is coupled to a tracer.

Figure 6:
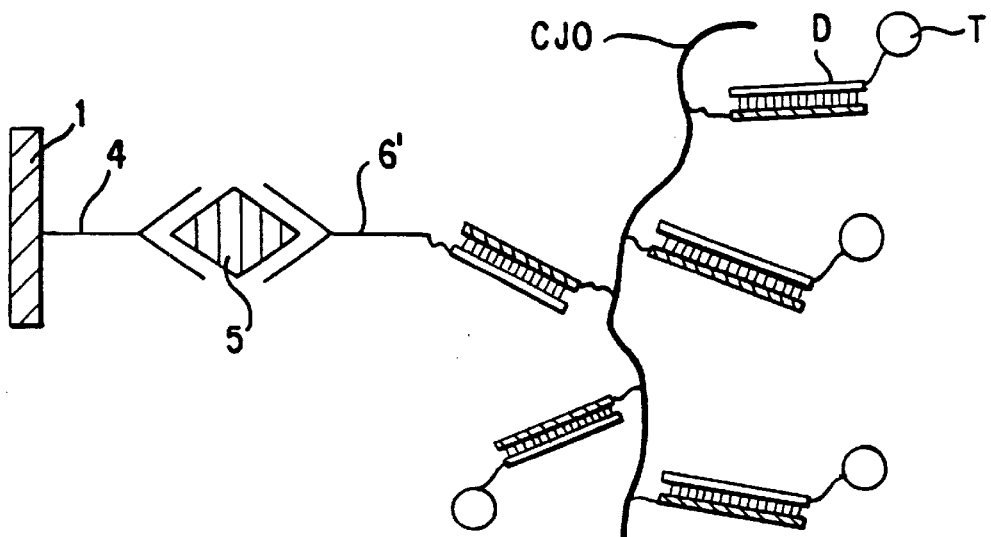

FIG. 6 depicts a specific sandwich immunological protocol which uses a detection conjugate reagent according to the invention.

1 represents the solid support.

4 represents a first, capturing, antibody, which is fixed to the solid support by some suitable means.

5 represents an antigen.

6' represents a second, detection, antibody, which is coupled covalently to a nucleotide sequence of interest (represented by a white rectangle).

CJO represents the copolymer-oligonucleotide conjugate. The oligonucleotide unit (represented by a black rectangle), which is attached to the copolymer, is complementary to the sequence of interest (represented by a white rectangle), which is attached to the second antibody.

D represents the detection probe, which is homologous to the oligonucleotide of the conjugate.

Figure 7:
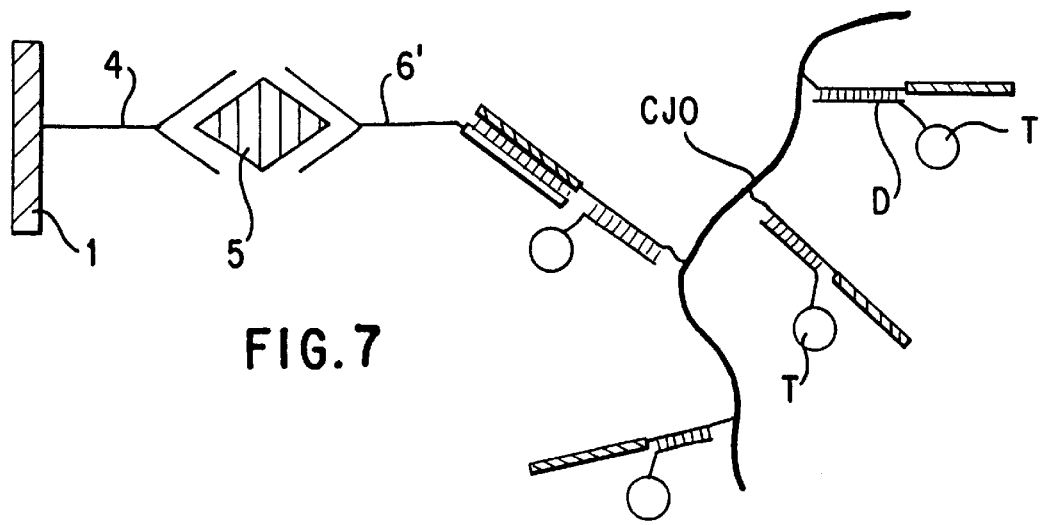

FIG. 7 is the equivalent for immunological detection to FIG. 3 for detecting nucleic acids.

Figure 8:
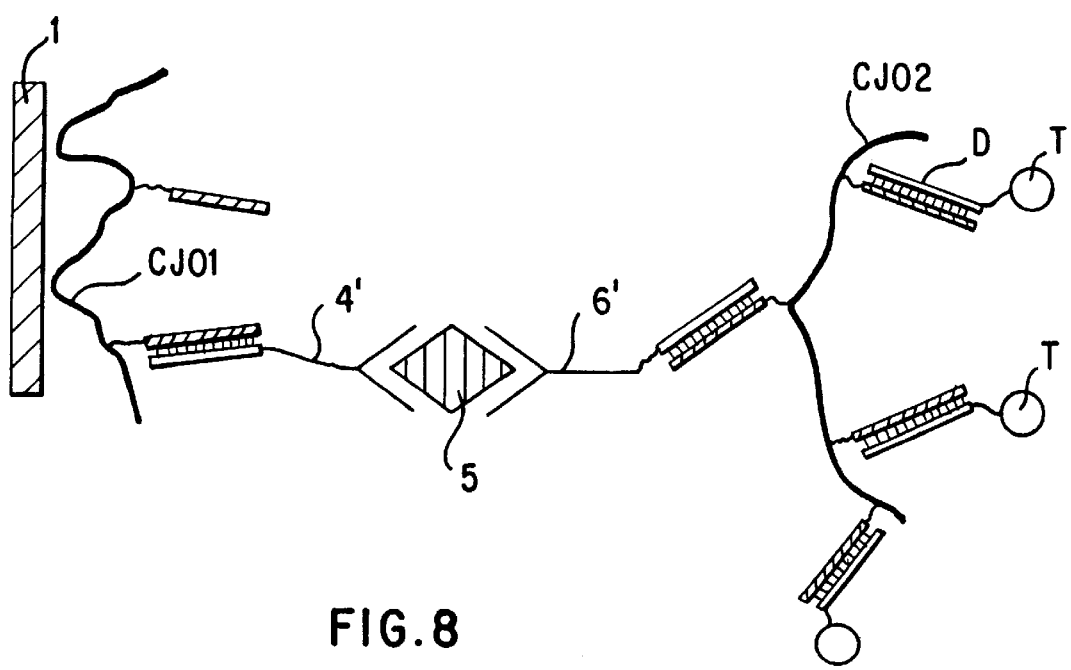

FIG. 8 is the equivalent for immunological detection to FIG. 4 for detecting nucleic acids.

The capturing antibody is attached to an oligonucleotide which is or is not identical to the sequence of interest, which is coupled to the antibody 6', and forms the compound 4'.

4' is captured on the solid phase by a capturing conjugate CJO1.

EXAMPLE 1
Synthesis and Characterization of the Copolymers

The following protocol constitutes the general mode of operation for the copolymerization reactions.

Table 1 will subsequently summarize the specific conditions for this synthesis.

50 ml of anhydrous N-dimethylformamide (ALDRICH; Cat. No. 22705-6), a quantity x, expressed in grams (g), of freshly distilled N-vinylpyrrolidone (ALDRICH; Cat. No. V 340-9) and also a quantity y (in grams) of N-acryloxysuccinimide (KODAK; Cat. No. 110 1690) are mixed in a 100 ml three-necked round-bottomed flask which has been purged with nitrogen.

The reaction medium, brought to a temperature of 60° C., is stirred for 2 hours while regularly bubbling through nitrogen in order to eliminate any trace of oxygen.

z g of 4,4'-azobis(4-cyanopentanoic acid) (FLUKA; Cat. No. 11 590) are dissolved in 1 ml of anhydrous N,N-dimethylformamide. This compound constitutes the initiator for the free radical polymerization reaction.

After bubbling through nitrogen for 15 minutes, the initiator solution is added rapidly to the reaction medium. This constitutes time zero for the polymerization.

The reaction is carried out at 60° C., with stirring, and while bubbling in nitrogen slowly and regularly.

Samples are removed every 3 minutes.

In order to stop the reaction, a few grains of a polymerization inhibitor: hydroquinone (JANSSEN; Cat. No. 123-31-9) are added. The samples are then placed in ice.

Each of these samples is then analysed by gas chromatography (DI 200 chromatograph, Enica 21 integrator, from DELSI INSTRUMENTS), using an SE 30 column (methylsilicone adsorbed onto 10% Chromosorb). This makes it possible to follow the polymerization reaction kinetically, that is to know, at any moment, the quantity of monomers remaining, and therefore the degree of conversion (relative to each monomer and globally).

Analytical conditions:

Air pressure=$H_2O$ pressure=1 bar ($10^5$ Pa)

$N_2$ pressure=0.8 bar

Oven temperature=175° C.

Injector temperature=detector temperature=300° C.

After a reaction time, which is noted down as t and expressed in hours, the reaction medium is poured into a separating funnel and then added, drop by drop, into a beaker which contains a large excess of ethyl ether (SDS, Cat. No. 440516), while stirring vigorously.

The polymer which has been formed during the reaction precipitates in the form of rather fine white crystals.

When all the reaction medium has been precipitated, the ethyl ether solution is filtered through a No. 4 frit. The polymer is washed with a large excess of ethyl ether and then dried for several hours in a vacuum oven at room temperature.

In order to purify the polymer (elimination of residual monomers and also of products of low molecular weight), the latter is dissolved in N,N-dimethylformamide (DMF) and then reprecipitated in ethyl ether.

The copolymers thus obtained are stored under an inert atmosphere in the absence of moisture.

The compound which has been formed has the following structure:

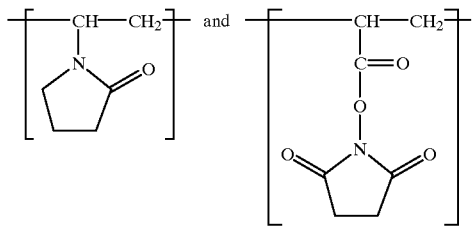

Table 1 summarizes the specific conditions for each polymerization reaction

TABLE 1

| Copolymer designation | xNVP grams | yNAS grams | C(*) moles/l | zAZCB gram | t hours | R(**) % |
|---|---|---|---|---|---|---|
| COPO1 | 2.22 | 0.84 | 0.5 | 0.074 | 20 | 55 |
| COPO2 | 2.78 | 4.22 | 1.0 | 0.148 | 20 | 90 |
| COPO3 | 1.14 | 2.54 | 0.5 | 0.074 | 20 | 90 |
| COPO4 | 0.23 | 0.50 | 0.1 | 0.015 | 20 | 90 |
| COPO5 | 2.28 | 5.08 | 1.0 | 0.148 | 20 | 90 |

(*)C represents the concentration of the monomers, in moles/liter, at the beginning of the reaction.
(**)R represents the conversion, expressed in percentage by weight, of the 2 starting monomers.
Abbreviations employed in Table 1
NVP = N-vinylpyrrolidone
NAS = N-acryloxysuccinimide
AZCB = 4,4'-azobis(4-cyanopentanoic acid)

The characteristics of the copolymers employed in the present invention are summarized in Table 2.

TABLE 2

|  | Molecular weight (g/mol)(*) | Molar % of NAS in the final copolymer(**) |
|---|---|---|
| COPO1 | 60,000 (10%) | 39 |
| COPO2 | 160,000 (2%) | 57 |
| COPO3 | 70,000 (2%) | 62 |
| COPO4 | 19,500 (2%) | 59 |
| COPO5 | 160,000 (2%) | 61 |

(*)The molecular weights were determined by light scattering (static method). Solvent employed: DMS/water = 90/10. Temperature: 20° C. The number in brackets represents the error in measuring the weight.
(**)This value was determined by measuring the N-hydroxysuccinimide (NHS) functions in the presence of an excess of $NH_4OH$ by UV spectroscopy at 260 nm using a molar extinction coefficient for NHS of 7100 l. $mol^{-1}$. $cm^{-1}$ in a water/DMF/$NH_4OH$ (0.1M) = 80/10/10 mixture.

The measurement error is 5%.

Table 3 gives the chemical shifts, determined by nuclear magnetic resonance (NMR) of the different carbons of the copolymer. The carbons are identified by the number depicted in the diagram below:

TABLE 3

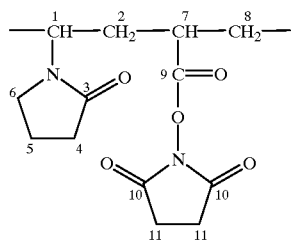

| Position of the carbon | Chemical shift |
|---|---|
| 1 | 48 (broad band) |
| 2 | 34 (broad band) |
| 3 | 175–177.5 (multiplet) |
| 4 | 32.2 (broad band) |
| 5 | 10 (singlet) |
| 6 | 42 (broad band) |
| 7 | 38.5 (broad band) |
| 8 | 34 (broad band) |
| 9 and 10 | 171 and 170.9 (doublet) |
| 11 | 26.4 and 26.65 (doublet) |

Solvent: deuterated DMF
Internal reference: dioxane with a band at 67.8 ppm.
The chemical shifts are given in parts per million (ppm).

Coupling of Oligonucleotide Units onto the Copolymers

The polynucleotides employed in the present invention are synthetic oligodeoxyribonucleotides prepared using a model 394 Applied Biosystems automated synthesizer in accordance with the manufacturer's instructions.

These oligonucleotides possess, at their 5' end, an aliphatic $NH_2$ arm which is prepared by the method described in Patent Application WO 91/19812.

By way of the ester functions of the N-hydroxysuccinimide, there is a direct reaction with the aminated arm at the 5' end of the oligonucleotide in order to form an amide bond.

The general coupling protocol is as follows:

An aqueous solution containing 32 nmoles of oligonucleotide is poured into an Eppendorf tube and then evaporated in a centrifugal evaporator in vacuo.

The dry residue is taken up in 50 microliters of 0.1 M borate buffer, pH 9.3, and 400 microliters of DMF are then added.

50 microliters of a 1 mg/ml solution of the copolymer in DMF (SDS, Cat. No. 340216) are added to this solution.

The Eppendorf tube containing the reaction medium is shaken for 16 hours in a heated shaker for Eppendorf tubes which has been brought to a temperature of 37° C.

The (DMF/water) mixture is subsequently evaporated in a centrifugal evaporator in vacuo.

The dry residue is taken up in 50 microliters of distilled water for analysis by capillary electrophoresis.

Experimental Conditions for Separation by Capillary Electrophoresis in Free Solution Apparatus: 270 A-HT marketed by Applied Biosystems
Silica capillary of 72 cm in length (Applied Biosystems, Cat. No. 0602-0014)
Separation electrolyte: 50 mM sodium carbonate buffer, pH 9.6
Voltage applied: 20 kilovolts.
Temperature: 40° C.
Injection at the anode.
Detection at the cathode, by UV spectroscopy at 260 nm (wavelength at which the oligonucleotide absorbs maximally).

The copolymer-oligonucleotide conjugate is then purified by permeation gel chromatography (PGC) under the following conditions:

Waters Ultra Hydrogel 500 column.
0.1 M phosphate buffer, pH 6.8.
Detection by UV spectroscopy at 260 nm.
Flow rate 0.5 ml/min.

After purification, the conjugate, in saline solution, is dialysed overnight at +4° C. in order to remove the salt. The water is removed by centrifugal evaporation in vacuo. The dry residue is taken up in 1 ml of distilled water and stored in a freezer at −20° C.

The list of oligonucleotides employed for coupling to a copolymer is given below.

The characteristics of the copolymer-oligonucleotide conjugates are given in Table 4:

TABLE 4

| Conjugate | Copolymer | Name employed for oligo-nucleotide | SEQ ID NO (a) | Yield (b) | Tr (c) | Me (d) | Concentration (e) |
|---|---|---|---|---|---|---|---|
| CJOA | COPO3 | 1844 | 1 | 41 | 9.6 | 9.9 | 2.5 |
| CJOB | COPO3 | 1978 | 2 | 52 | 9.6 | 9.9 | 3.8 |
| CJOC | COPO3 | 1854 | 3 | 48 | 10.1 | 10.1 | 8.7 |

(a) The oligonucleotides have the following sequences (from 5' to 3'):

```
SEQ ID NO1:
TCATCCACCT GGCATTGGAC TGCCATAACC ATGAGTG      37

SEQ ID NO2:
TACTCACCAG TCACAGAAAA GC                      22

SEQ ID NO3:
GATGAGCTAT ATGAGAACGG TA                      22
```

These oligonucleotides possess, at their 5' end, an aliphatic arm having an $NH_2$ function, which arm is prepared by the method described in Patent Application WO 91/19812.

(b) The coupling yield, calculated by integrating the GPC peaks, is the ratio, by HPLC, of the area of the peak of the conjugate to the sum of the areas of the peaks of the conjugate and of the uncoupled oligonucleotide. It is given in %.

(c) Tr represents the GPC retention time under the conditions described in the preceding paragraph. It is given in minutes.

(d) Me represents the retention time, given in minutes, under the capillary electrophoresis separation conditions described in the preceding paragraph.

(e) The concentration of the oligonucleotide is given in picomoles per microliters, as determined by UV spectrometry, by measuring the absorbance at 260 nm and knowing the molar extinction coefficient of the oligonucleotide at this wavelength.

EXAMPLE 2

Detection of a Nucleic Acid Fragment by a Sandwich Protocol Using Oligonucleotides Coupled to Copolymers for Detection Amplification A PCR was carried out in accordance with the standard protocol as described in "PCR PROTOCOLS: a guide to methods and applications", edited by M. A. Innis, D. H. Gelfand, J. J. Sninsky, T. J. White, Academic Press. The target is a DNA plasmid, pBR 322 (Cat. No. D4904, SIGMA), which contains 4363 base pairs.

The plasmid is in solution in a 10 mM Tris buffer, pH 8.0. The two primers employed for the amplification are TEM1 (SEQ ID NO: 4) and TEM2 (SEQ ID NO: 5):

```
SEQ ID NO: 4:
CCCCGAAGCGTTTTC                15

SEQ ID NO: 5:
CGGTATGGTTTGCTGCT              17
```

The PCR fragment which is produced is checked on a 5% acrylamide gel. It contains 347 base pairs.

The PCR fragment is denatured before use by adding 10 microliters of 2N sodium hydroxide solution to 100 microliters of the solution containing the fragment. The whole is neutralized 5 minutes later by adding 10 microliters of 2N acetic acid.

100 microliters of a solution of oligonucleotide 1978 (SEQ ID NO: 2) at a concentration of 150 nM in 3×PBS buffer (0.15 M sodium phosphate, 0.45 M sodium chloride, pH 7.5) are deposited in two NUNC polystyrene microtitration plates (Cat. No. 439454). The plates are incubated for two hours at a temperature of 37° C.

After the plates have been washed 3 times with 300 microliters of PBS-Tween buffer (50 mM sodium phosphate, 150 mM sodium chloride, containing 0.5 ml/l Tween 20, MERCK Cat. No. 822184), 100 microliters of denatured PCR fragment, diluted in PEG buffer (0.1 M sodium phosphate, 0.5 M sodium chloride, pH 7.0, containing 0.14 mg/ml of salmon DNA and 20 g/l of PEG 4000, MERCK Cat. No. 807490, and 6.5 g of Tween 20, BIORAD Cat. No. 170-6531) are added to the wells of the microtitration plates. The plates are incubated at 37° C. for one hour and then washed 3 times with 300 microliters of PBS-Tween.

100 microliters of detection probe, oligonucleotide 1844 (SEQ ID NO: 1) coupled to alkaline phosphatase, at an oligonucleotide concentration of 15 nM in PEG buffer, are added to each well of one of the plates. The detection probe, 1844, contains a sequence which is complementary to the PCR target. It is labelled with alkaline phosphatase (akp), as described in Patent Application WO 91/19812. The plate is incubated at 37° C. for one hour and then washed 3 times with 300 microliters of PBS-Tween. This plate corresponds to a direct sandwich protocol.

In parallel, 100 microliters of an oligonucleotide-copolymer conjugate, CJOA, in PEG buffer, are added to each well of the second microtitration plate. This conjugate is an intermediary in the sandwich system which makes it possible to increase the sensitivity. The plate is incubated at 37° C. for one hour and then washed 3 times with 300 microliters of PBS-Tween. 100 microliters of the detection probe, oligonucleotide 1841 (SEQ ID NO: 6) coupled to alkaline phosphatase, at an oligonucleotide concentration of 15 nM in PEG buffer, are added to each well of the plate. This plate corresponds to a protocol using signal amplification by way of the copolymer-oligonucleotide.

```
SEQ ID NO: 6:
GTCCAATGCC AGGTGGATGA          20
```

The detection probe is complementary to a portion of oligonucleotide 1844, which is coupled to the copolymer. It is labelled with alkaline phosphatase as described in Patent Application WO 91/19812.

The plate is incubated at 37° C. for one hour and then washed 3 times with 300 microliters of PBS-Tween.

The 2 plates are then treated in an identical manner.

100 microliters of PNPP substrate (para-nitrophenyl phosphate, SIGMA Cat. No. N 2765) are added to each well; for this, a tablet of 20 mg of substrate is dissolved in 10 ml of 1M diethanolamine, 0.5 mM $MgCl_2$ buffer, pH 9.8. After a reaction time of 20 minutes, enzymic activity is stopped by adding 100 microliters of 1N NaOH.

The optical density is read at a wavelength of 405 nm on a BIOMERIEUX AXIA MICROREADER plate reader.

The results (optical density values) obtained are summarized in Table 5 below:

TABLE 5

| Dilution of the PCR | Direct sandwich detection | Detection using oligonucleotide-copolymer |
|---|---|---|
| 0 | 12 | 10 |
| dil 1/100 000 | 12 | 15 |
| dil 1/10 000 | 10 | 16 |
| dil 1/1000 | 11 | 30 |
| dil 1/100 | 20 | 137 |
| dil 1/10 | 160 | 1110 |

The measurement error is approximately 10%.

The values obtained correspond to optical density units measured on an AXIA MICROREADER (AXIA is a BioMérieux trade mark).

The well which does not contain any PCR fragment (0) serves as the negative control. Using the direct system (without amplification), the PCR fragment is detected at a 1/10 dilution. Using the copolymer-oligonucleotide system, the PCR fragment is detected at a dilution of less than 1/100, with the signal obtained being multiplied by a factor of 10. The sensitivity of the test is increased by a factor greater than 10. The background noise is not increased by the signal amplification.

EXAMPLE 3
Detection of a Nucleic Acid Fragment by a Sandwich Protocol Using Oligonucleotides Coupled to Copolymers for Detection and for Capturing The protocol is identical to that of Example 2, except for the fact that the conjugate CJOB (oligonucleotide 1978 (SEQ ID NO: 2) coupled to copolymer COPO3), at an oligonucleotide concentration of 150 nM in 3×PBS, is added to each well of one of the microtitration plates, as capturing probe, in place of oligonucleotide 1978.

The copolymer CJOA is employed as a detection amplification system as in Example 2.

The other plate, which is to serve as a control for measuring the increase in sensitivity, is prepared in the same manner as in Example 2 (direct detection).

The results (optical density values) obtained are summarized in Table 6:

TABLE 6

| Dilution of the PCR | Direct sandwich detection | Detection using 2 copolymers for capturing and for detection |
|---|---|---|
| 0 | 10 | 70 |
| dil 1/100 000 | 10 | 90 |
| dil 1/10 000 | 11 | 101 |
| dil 1/1000 | 21 | 298 |
| dil 1/100 | 28 | 705 |
| dil 1/10 | 198 | >2500 |

The measurement error is approximately 10%.

The values obtained correspond to optical density units measured on an AXIA MICROREADER (AXIA is a BioMérieux trade mark).

The value of 2500 corresponds to the saturation value for the microplate reader.

The well which does not contain any PCR fragment (0) serves as the negative control. Using the oligonucleotide-phosphatase system (without amplification), the PCR fragment is detected at a 1/10 dilution. Using the copolymer-oligonucleotide system for capturing and for detection, the PCR fragment is detected at a 1/1000 dilution. The sensitivity of the test is increased by a factor of 100.

If this improvement is compared with that obtained in Example 2, which was approximately 10-fold, it appears that the combination of two oligonucleotide-bipolymer conjugates at one and the same time for detection and for capturing gives an even more impressive result, not only as regards the increase in sensitivity but also as regards the signal to background noise ratio.

EXAMPLE 4
Detection of Alpha-Foetoprotein (AFP) by a Sandwich Protocol Using a Copolymer-Oligonucleotide as a Detection Intermediary in Order to Increase the Signal The increase in sensitivity is assessed by comparison with a conventional immunological sandwich protocol.

100 microliters of a solution of an anti-alpha-foetoprotein monoclonal antibody (BIOMERIEUX Cat. No. P3F11G9), diluted to a concentration of 10 micrograms/ml in 50 mM sodium carbonate buffer ($Na_2CO_3$, PROLABO 27771290; $NaHCO_3$, PROLABO 27778293), pH 9.6, are added to two NUNC polystyrene microtitration plates, Cat. No. 439454. The plates are incubated for two hours at a temperature of 37° C. The two plates are then washed with 300 microliters of 1×PBS buffer (50 mM sodium phosphate, 150 mM sodium chloride, containing 0.5 ml/l of Tween 20, MERCK Cat. No. 822184).

50 microliters of alpha-foetoprotein antigen (BEHRING Cat. No. OTOD 02/03), diluted in PBS-Tween buffer containing 10% horse serum, and 50 microliters of a second goat anti-alpha-foetoprotein polyclonal antibody (BIOMERIEUX Cat. No. CH109-1981), coupled by conventional methods to peroxidase (Boehringer Mannheim, Cat. No. 814393), at a concentration of 2 mg/l in PBS-Tween buffer containing 10% horse serum, are added to each well of one of the plates (conventional immunological sandwich). The plate is incubated at 37° C. for one hour and then washed 3 times with 300 microliters of PBS-Tween.

In parallel, 50 microliters of alpha-foetoprotein antigen (BEHRING Cat. No. OTOD 02/03), diluted in PBS-Tween buffer containing 10% horse serum, and then 50 microliters of the second anti-alpha-foetoprotein polyclonal antibody (BioMérieux Cat. No. CH109-1981), coupled to an oligonucleotide 1614 (SEQ ID NO7) and diluted in PEG buffer (0.1M sodium phosphate, 0.5M sodium chloride, pH 7.0, containing 0.14 mg/ml salmon DNA, 20 g/l PEG 4000 (MERCK Cat. No. 807490) and 6.5 g of Tween 20 (BIORAD Cat. No. 170-6531)) are added to the second plate (detection using signal amplification).

The concentration of antibody in the PEG solution containing antibody coupled to oligonucleotide 1614 is 2 mg/l.

SEQ ID NO: 7:
TACCGTTCTCATATAGC          17

The antibody and oligonucleotide 1614 are coupled together using the same method as described for coupling oligonucleotide to peroxidase in Patent Application WO 91/19812.

The plate is incubated at 37° C. for one hour and then washed 3 times with 300 microliters of PBS-Tween. 100 microliters of a solution of an oligonucleotide-copolymer conjugate, CJOC, at an oligonucleotide concentration of 150 nM in PEG buffer, are added to the wells of the microtitration plate. The plate is incubated at 37° C. for one hour and is then washed 3 times with 300 microliters of PBS-Tween.

100 microliters of the detection probe oligonucleotide 1614 (SEQ ID NO: 7) coupled to peroxidase (Patent Application WO 91/19812), at an oligonucleotide concentration of 15 nM in PEG buffer, are added to each well of the plate. The plate is incubated at 37° C. for one hour and is then washed 3 times with 300 microliters of PBS-Tween.

The enzymic activity is detected in the same way for both plates.

100 microliters of OPD (ortho-phenylenediamine, SIGMA Cat. No. P7288) substrate solution are added to each well. In order to prepare this solution, one tablet of 20 mg of substrate is dissolved in 10 ml of citrate buffer, pH 4.93 (0.055 M citric acid, 0.1 M $Na_2 HPO_4$). After a 15-minute reaction at 37° C., the enzymic activity is stopped by adding 100 microliters of 1N sulphuric acid.

The optical density is read at a wavelength of 492 nm on a BIOMERIEUX AXIA MICROREADER plate reader.

The results (optical density values) obtained are summarized in Table 7:

TABLE 7

| Concentration of AFP antigen (ng/ml) | Conventional immunological detection | Copolymer-oligo-nucleotide for detection |
|---|---|---|
| 0 | 55 | 110 |
| 0.05 | 60 | 110 |
| 0.10 | 60 | 250 |
| 0.50 | 60 | 420 |
| 1.0 | 120 | 670 |
| 2.5 | 250 | 1620 |
| 5.0 | 370 | >2500 |
| 10.0 | 630 | >2500 |

The measurement error is approximately 10%.

The values obtained correspond to optical density units measured on an AXIA MICROREADER (AXIA is a BioMérieux trade mark).

The value of 2500 corresponds to the saturation value for the microplate reader.

The results obtained demonstrate that the sensitivity of the test is increased very greatly by using the copolymer-oligonucleotide. With the amplification system employing the copolymer-oligonucleotide, it is possible to detect 0.1 ng/ml alpha-foetoprotein, with the signal obtained being increased by a factor of 2 with respect to the well which does not contain any antigen (well 0). Without amplification (conventional immunological detection), the detection of AFP begins at 1 ng/ml.

In this example, the detection antibody is a polyclonal antibody.

EXAMPLE 5
Detection of Alpha-Foetoprotein by a Sandwich Protocol Using Oligonucleotides Coupled to Copolymers for Detection and/or for Capturing The increase in sensitivity is assessed in comparison to a conventional immunological sandwich protocol.

The conventional immunological sandwich protocol is carried out in the same manner as that described in Example 4, except that a monoclonal antibody (BioMérieux Cat. No. P7H10B7) coupled to peroxidase is employed for detection in place of the polyclonal antibody (BioMérieux Cat. No. CH109-1981).

The protocol employing oligonucleotides coupled to copolymers for detection is identical to that in Example 4, except that a monoclonal antibody (BioMérieux Cat. No. P7H10B7) is used for detection in place of the polyclonal antibody (BioMérieux Cat. No. CH109-1981).

The protocol employing oligonucleotides coupled to copolymers for detection and for capturing is as follows:

100 microliters of an oligonucleotide-copolymer conjugate, CJOA, at an oligonucleotide concentration of 150 nM in 3xPBS buffer, are added to a microtitration plate. The plate is incubated at 37° C. for two hours and then rinsed 3 times with 300 microliters of PBS-Tween.

100 microliters of anti-alpha-foetoprotein monoclonal antibody (BIOMERIEUX Cit. No. P3F11G9), coupled, as described in Example 4, to oligonucleotide 1841 (SEQ ID NO: 6), are then added. This antibody coupled to oligonucleotide 1841 is diluted in PEG buffer to an antibody concentration of 2 mg/l. The plate is incubated at 37° C. for one hour and then washed 3 times with 300 microliters of PBS-Tween.

The AFP antigen, and then monoclonal antibody (BioMérieux Cat. No. P7H10B7) coupled to an oligonucleotide 1614 (SEQ ID NO: 7), are added as described in Example 4.

The reaction steps with the conjugate CJOC, and with oligonucleotide 1614 coupled to peroxidase, and the detection step using the substrate OPD, are identical to those in Example 4.

The results (optical density values) obtained are summarized in Table 8:

TABLE 8

| Concentration of AFP antigen (ng/ml) | Conventional immunological detection | Copolymer-oligonucleotide for detection | Copolymer-oligo-nucleotide for capturing and detection |
|---|---|---|---|
| 0 | 33 | 155 | 110 |
| 1 | 35 | 175 | 250 |
| 5 | 70 | 651 | 650 |
| 10 | 140 | 1230 | 1425 |
| 50 | 545 | >2500 | >2500 |
| 100 | 1025 | >2500 | >2500 |

The measurement error is approximately 10%.

The values obtained correspond to optical density units measured on an AXIA MICROREADER (AXIA: BioMérieux trade mark).

The value of 2500 corresponds to the saturation value for the microplate reader.

A considerable increase in sensitivity is observed in comparison with conventional immunological detection and with the use of a copolymer-oligonucleotide for detection. The trend of the results is in the same direction as in Example 4 with, in this case, a monoclonal antibody being used for detection in place of a polyclonal antibody. The signal/noise ratio for an AFP quantity of 5 ng/ml is approximately 2 for the conventional immunological detection while it is 4.2 for the copolymer-oligonucleotide system used for detection.

As demonstrated previously for the nucleic acids in Example 3, an improvement in sensitivity is observed when a copolymer-oligonucleotide is used for detection and for capturing.

Thus, for an AFP concentration of 1 ng/ml, the signal/noise ratio is 2.3, thereby making it possible to detect this concentration.

This result is obtained, inter alia, due to a reduction in the background noise, thereby demonstrating the importance of the method, since background noise is a basic problem in all signal amplification systems.

As a general rule, the background noises observed using an oligonucleotide-bipolymer for detection and/or for capturing are low (see Examples 2 to 4).

EXAMPLE 6
Influence of the Number of Oligonucleotides Coupled to the Copolymer-Oligonucleotide Conjugate for Detection Amplification In the method described, amplification of the signal is directly related to the number of oligonucleotides attached to the copolymer.

Thus, in the conventional sandwich method, one detection probe carrying a single tracer, for example an enzymic tracer, is able to hybridize to one target molecule which is hybridized to a capturing probe.

When a copolymer-oligonucleotide is employed as an intermediary probe, the number of detection probes, and therefore the number of tracers, which are capable of hybridizing with one target molecule is, in theory, equal to the number of probes which are coupled to the copolymer minus one (that which hybridizes to the target).

Attachment of a Variable Number of Oligonucleotides to one Copolymer

An aqueous solution containing 15 nmoles of oligonucleotide 12 (SEQ ID NO: 8) is evaporated to dryness in a 1.5 ml Eppendorf tube.

```
SEQ ID NO: 8:
TCATCCACCT GGCATTTGGAC         20
```

The dry residue is dissolved in $x_1$ microliters of 0.1 M borate buffer, pH 9.3. $y_1$ microliters of DMF and then $z_1$ microliters of the copolymer COPO3 (Table 1), at 1 mg/ml in DMF, are then added to the solution. After 3 hours of reaction at 37° C., the solvent is removed in vacuo in an evaporator. The dry residue is dissolved in 50 microliters of water and analysed by gel permeation under the conditions described in Example 1.

Table 9 summarizes the coupling conditions for the different conjugates prepared, and Table 10 summarizes the characteristics of the conjugates which were prepared.

TABLE 9

| Conjugates | $x_1$ | $y_1$ | $z_1$ | Stoichiometry |
|---|---|---|---|---|
| CJOD1 | 30 | 255 | 15.0 | 1/4 |
| CJOD2 | 30 | 248 | 22.5 | 1/6 |
| CJOD3 | 30 | 225 | 45 | 1/12 |
| CJOD4 | 30 | 180 | 90 | 1/24 |
| CJOD5 | 30 | 45 | 225 | 1/60 |
| CJOD6 | 42 | 0 | 375 | 1/100 |

The stoichiometry S represents the ratio between the number of moles of oligonucleotides Introduced and the number of moles of NHS functions available for the coupling.

TABLE 10

| Conjugates | Coupling yield Y | Retention time | N | Concentration |
|---|---|---|---|---|
| CJOD1 | 49 | 9.80 | 31.5 | 3.4 |
| CJOD2 | 53 | 9.66 | 22.7 | 4.5 |
| CJOD3 | 57 | 9.72 | 12.2 | 5.8 |
| CJOD4 | 59 | 9.51 | 6.3 | 5.4 |
| CJOD5 | 55 | 9.70 | 2.4 | 5.3 |
| CJOD6 | 60 | 9.50 | 1.6 | 4.6 |

The HPLC retention time (in minutes), the coupling yield Y (in %), and the concentration (in nmmoles/ml) of the conjugates, are calculated in the same manner as in Table 4 of Example 1.

N represents the number of moles of oligonucleotides per mole of copolymer. The theoretical number, Nt, of oligonucleotides per chain is calculated from a knowledge of the stoichiometry S of the reaction by comparison with the number of NHS functions which are available on the copolymer (257 functions for COPO3: see Table 2); $Nt=257 \times S$.

N is calculated in accordance with the formula:

$$N = Nt \times Y.$$

Comparison of the Efficacy of the Different Conjugates in Detection Amplification The increase in sensitivity is measured while comparing protocols using the different oligonucleotide-copolymer conjugates as detection intermediates. A reference assay without any copolymer-oligonucleotide as intermediate is carried out as described in Example 2 (direct sandwich detection).

The protocol involving signal amplification by means of a copolymer-oligonucleotide intermediate is identical to that described in Example 2 except that the capturing oligonucleotide added to the bottom of the plate is oligonucleotide 474 (SEQ ID NO: 9).

```
SEQ ID NO: 9:
AAAAAAAAAA AAAAAAAAAA AAAAAAAAAA         30
```

The target is not a PCR fragment but, instead, a single-stranded synthetic oligonucleotide 469 (SEQ ID NO: 10); the latter does not, therefore, need to be denatured with sodium hydroxide solution.

```
SEQ ID NO: 10:
TTTTTTTTTT TTTTTTTTTT GTCCAATGCC AGGTGGATGA   40
```

This target is diluted with PEG buffer to give concentrations from 5000 pg/ml to 1 pg/ml.

One part of this target is complementary to oligonucleotide 12, which is attached to the copolymer, and another part is complementary to oligonucleotide 474.

The different copolymers CJOD1 to CJOD6 are added in parallel to the wells of the microtitration plate.

The detection probe is oligonucleotide 1841 (SEQ ID NO: 6) coupled to horseradish peroxidase.

The substrate of the enzyme is OPD, as described in Example 4, with reading being carried out at 492 nm on an AXIA MICROREADER plate reader (AXIA, is a BIOMERIEUX trade mark).

Direct Sandwich Protocol

Capture by oligonucleotide 474 (SEQ ID NO: 9)

Synthetic target 469 (SEQ ID NO: 10)

Detection with detection probe 12 (SEQ ID NO: 8), labelled with peroxidase.

Table 11 summarizes the results obtained with the different copolymer-oligonucleotides.

TABLE 11

| Concentration of target (pg/ml) | CJOD1 | CJOD2 | CJOD3 | CJOD4 | CJOD5 | CJOD6 | Direct |
|---|---|---|---|---|---|---|---|
| 5000 | 2500 | 2500 | 2500 | 2500 | 2500 | 2500 | 2500 |
| 1000 | 2500 | 2500 | 2500 | 2500 | 2500 | 1536 | 601 |
| 500 | 2500 | 2500 | 2500 | 2500 | 1461 | 995 | 370 |
| 50 | 1661 | 1253 | 1213 | 590 | 549 | 480 | 5 |
| 5 | 627 | 543 | 455 | 243 | 185 | 184 | 0 |
| 1 | 519 | 458 | 332 | 206 | 0 | 0 | 0 |

The measurement error is approximately 10%.

The values obtained correspond to optical density units measured on an AXIA MICROREADER (AXIA: BioMérieux trade mark).

The background noise determined for each conjugate in an assay without target is subtracted from the values obtained for the different conjugates at the different target concentrations.

It is to be noted that the number of moles of oligonucleotide per mole of copolymer relates to the increase obtained in signal amplification. The values obtained for the lowest concentration of target, of 1 pg/ml, increase in size as the number of oligonucleotides attached to the copolymer increases. This concentration of target is not detected with CJOD5 and CJOD6, in which only 1.6 and 2.4 oligonucleotides, respectively, are present per mole of copolymer.

Even with these latter conjugates, there is an increase in sensitivity as compared with direct sandwich detection.

EXAMPLE 7

Synthesis and Characterization of Conjugates Having Copolymers Based on AMVE

Definition of the AMVE Copolymer

The AMVE copolymer employed is a copolymer of maleic anhydride and methyl vinyl ether, marketed by Polyscience under Cat. No. 03102. Its molecular weight is 67,000 and it is an alternating copolymer consisting of 50% of each of the two monomeric units.

Protocol for Coupling Oligonucleotides to the AMVE Copolymer 25 nmoles of oligonucleotide are dried in a centrifugal evaporator in vacuo and then dissolved in 7 microliters of 0.1 M sodium borate, 0.5 M NaCl, buffer, pH 9.3. 143 microliters of anhydrous dimethyl sulphoxide and then 10 microliters of copolymer solution in anhydrous dimethyl sulphoxide, at a concentration of 15 g/l for conjugates CJOE, CJOG and CJOI, or 5 g/l for conjugates CJOF, CJOH and CJOI, are subsequently added to this solution. After shaking for 6 h at 37° C., 100 microliters of 100 mM sodium hydrogen carbonate buffer, pH 8.2, are added to the reaction medium and allowed to react for 30 minutes in order to hydrolyse any sites on the copolymer which are still available. These solvents are removed in a centrifugal evaporator in vacuo, and the conjugates are then dissolved in 200 microliters of distilled water and purified by high performance liquid chromatography on a Waters Ultra Hydrogel 500 column in 0.1 M phosphate buffer, pH 6.8.

The results obtained are summarized in Table 12 below:

TABLE 12

| Conjugate | Name used for the oligonucleotide | SEQ ID NO (a) | Yield (b) | Tr (c) | Concentration (e) | N |
|---|---|---|---|---|---|---|
| CJOE | 1844 | 1 | 34 | 10.57 | 1.32 | 2 |
| CJOF | 1844 | 1 | 38 | 9.88 | 1.76 | 7 |
| CJOG | 1854 | 3 | 59 | 10.17 | 2.74 | 6 |
| CJOH | 1854 | 3 | 47 | 9.90 | 2.18 | 14 |
| CJOI | 1843 | 11 | 52 | 10.71 | 1.98 | 4 |
| CJOJ | 1843 | 11 | 30 | 9.87 | 1.39 | 7 |

N represents the number of oligonucleotides per copolymer chain.

(a) The sequence of oligonucleotide 1843 (SEQ ID NO: 11) is:

```
SEQ ID NO: 11:
CGCTTTTTTG CACAACATGG GGGATCATG          29
```

These oligonucleotides possess, at their 5' end, an aliphatic arm having an amine function, which arm is prepared by the method described in WO 91/19812.

(b) The coupling yield, calculated by integrating the GPC peaks, is the ratio, by HPLC, of the area of the peak of the conjugate to the sum of the areas of the peaks of the conjugate and of the uncoupled oligonucleotide. It is given in %.

(c) Tr represents the GPC retention time under the conditions described in Example 1. It is given in minutes.

(e) The concentration of the oligonucleotide is given in picomoles per microliter, as determined by UV spectrometry, by measuring the absorbance at 260 nm, knowing the molar extinction coefficient of the oligonucleotide at this wavelength.

EXAMPLE 8

NUNC (Maxisorb) microtitration plates are coated with an anti-alpha-foetoprotein monoclonal antibody (BioMérieux Cat. No. P3F11G9), which is diluted to 10 micrograms/milliliter in 0.05 M carbonate buffer, pH 9.7. The plates are then incubated, it being equally possible for the plates to be incubated for 2 hours at 37° C., for 18 hours at ambient temperature or for 56 hours at a temperature of +4° C. The excess of reagent is removed, and the plates are washed with a PBS-Tween buffer. 100 microliters of a one gram/liter solution of casein are then added to each well, and the plates are incubated at 37° C. for one hour and then washed as before. 50 microliters of Behring alpha-foetoprotein antigen solution, at various dilutions in PBS-Tween buffer containing 10% horse serum, are introduced into the wells, and 50 microliters of a solution of oligonucleotide 1614 (SEQ ID NO: 7) conjugate, which is complementary to the sequence of the CJOG or CJOH conjugate and is coupled to the anti-alpha-foetoprotein polyclonal antibody (BioMérieux Cat. No. CH109-1981) are added. This conjugate is diluted in a PBS-Tween buffer which contains 10% horse serum. After having incubated the plates for one hour at 37° C., and after having carried out washes with PBS-Tween, 100 microliters of copolymer-oligonucleotide conjugate solution, diluted in PEG buffer, are added to each well. After incubating the plates for one hour at 37° C., and then carrying out washings, 100 microliters of the solution of the detection probe: oligonucleotide 1841 (SEQ ID NO: 6)—peroxidase, in PEG are added to each well, and the plates are then incubated for an hour at 37° C. After having washed the plates free of excess reagent, 100 microliters of the solution of OPD substrate are introduced into each well. After developing for 7 minutes at room temperature, the reaction is stopped by adding 0.1 ml of a normal solution of sulphuric acid (see Example 4 for details).

The non-amplified, control plates are produced in identical manner except that the polymer step is omitted. The results which were obtained are recorded in Table 13 below:

TABLE 13

| AFP antigen (ng/ml) | Conventional immunological detection | Conjugate CJOG | Conjugate CJOH |
|---|---|---|---|
| 0 | 50 | 44 | 48 |
| 0.5 | 60 | 71 | 101 |
| 1 | 70 | 151 | 215 |
| 2.5 | 90 | 530 | 828 |
| 5 | 130 | 1600 | 2500 |
| 10 | 220 | 2500 | 2500 |
| 25 | 550 | 2500 | 2500 |
| 50 | 880 | 2500 | 2500 |

The measurement error is approximately 10%.

The values obtained correspond to optical density units measured on an AXIA MICROREADER (BioMérieux trade mark).

The value of 2500 corresponds to the saturation value for the microplate reader.

This example demonstrates a very substantial increase in sensitivity when an oligonucleotide-AMVE conjugate is employed as a detection intermediate. The concentration of AFP for which the signal/background noise ratio is greater than 2 is 5 ng/ml in the case of conventional immunological detection, 0.5 ng/ml in the case of the CJOG conjugate and 0.1 ng/ml in the case of CJOH. As in the case of the NVPNAS copolymer in Example 6, the gain in sensitivity is improved by increasing the ratio N, i.e. the number of moles of oligonucleotide per mole of copolymer. N is equal to 6 in the case of CJOG and equal to 14 in the case of CJOH.

EXAMPLE 9

Detection of a Nucleic Acid Fragment by Means of a Sandwich Protocol on an Automatic VIDAS Using Oligonucleotides Coupled to Copolymers for Detection and for Capture. Comparison of a 1-Step Protocol and a 2-Step Protocol A PCR is carried out, and the fragment is then denatured as described in Example 2.

The following protocol is carried out automatically on an automatic VIDAS (trade mark—marketed by BioMérieux SA-VITEK). The following steps are carried out automatically.

The reaction is conducted in a conical support termed an SPR ("solid-phase receptacle"), which conical support is produced from a material sold under the name K resin, which is a butadiene-styrene copolymer marketed by BioMérieux Vitek (U.S.A.). The various reagents are arranged in the strip and the different steps take place in the SPR, which acts as a pipette. The sandwich hybridization reaction described in the protocol below takes place on the internal surface of the cone.

The oligonucleotide 1978-copolymer (CJOB, Table 4) conjugate is attached passively to the internal surface of the SPR. The oligonucleotide concentration employed is 0.15 nmole/ml, in a 300 microliter volume of a 4×PBS solution (200 mM sodium phosphate, pH 7.0, 600 mM NaCl). After one night at room temperature, or two hours at 37° C., the cones are washed twice with a PBS-Tween solution and then dried in vacuo.

The strip contains all of the reagents which are required for the detection, in separate wells, i.e.:

well 2: 100 microliters of a 0.015 nmoles/ml solution of conjugate CJOA (1844 coupled to the NVPNAS copolymer) in a PEG buffer (150 mM sodium phosphate, 450 mM NaCl, pH 7.0, +0.14 mg/ml salmon sperm DNA (Sigma D 9156) +20 g/l of PEG 4000 (Merck 807490) +6.5 g/l of Tween 20 (Biorad 170-6531)), well 3: 200 microliters of a 0.045 nmoles/ml solution, in the PEG buffer, of the detection probe, oligonucleotide 1841-alkaline phosphatase. The detection probe is prepared as described in WO 91/19812.

wells 4 and 5: 2 times 600 microliters of PBS-Tween washing solution, well 6: 300 microliters of MUP substrate (4-methylumbelliferyl phosphate) in solution in a diethanolamine buffer.

200 microliters of the solution of the target (diluted PCR fragment), in a PEG buffer, are added to the first well (well 1) of the strip. After incubating the cone, by the mixture, which is reconstituted in well 2, of the target (110 microliters from well 1), the detection probe and the copolymer-oligonucleotide conjugate for amplification (110 microliters from well 3), for 45 minutes, it is then washed twice with a solution of PBS-Tween. 250 microliters of substrate are then aspirated into the cone, which is incubated for 15 minutes, after which the mixture is released into a reading cuvette. The apparatus measures the fluorescent signal of the cuvette, expressed in RFU (relative fluorescence units).

In parallel, a protocol is carried out which is identical except that it has 2 separated incubations. The first incubation, of 45 minutes, contains the neutralized PCR fragment and oligonucleotide 1844 coupled to an NVPNAS polymer. After washing, the 1841-alkaline phosphatase detection probe is incubated for 45 minutes.

The results are presented in Table 14.

TABLE 14

| Dilution of the PCR fragment | 2-step incubation | 1-step incubation |
| --- | --- | --- |
| 1/10 | 10060 | 8915 |
| 1/100 | 2960 | 1575 |
| 1/1 000 | 780 | 595 |
| 1/10 000 | 470 | 495 |
| 1/100 000 | 355 | 360 |
| 0 | 348 | 338 |

The detection levels are expressed in RFU (relative fluorescence units).

The measurement error is approximately 10%.

The background noise of the assay is determined by not adding target (assay 0).

This example demonstrates that the limit of detection is the same in both cases. It is therefore possible to achieve signal amplification by the detection copolymer without extending the manipulation time, and without increasing the background noise, by using a 1-step protocol. This example also demonstrates that it is possible to adapt the signal amplification to systems other than the microplate system, and, in particular, to a different type of solid phase, since the K resin of which the SPR cone is composed is different from that of the microplate, which is made of polystyrene.

We claim:

1. A kit for detecting at least one nucleic acid sequence of interest, with signal amplification, said kit having in suitable containers:
   a reagent; and
   a single species of tracer-labelled oligonucleotide probe reactive with said reagent;
   wherein said reagent comprises at least one linear backbone polymer molecule having a backbone chain formed by carbon-to-carbon covalent bonds, said at least one polymer molecule including at least one monomeric unit having a lateral substituent, said lateral substituent comprising an oligonucleotide unit that hybridizes with said sequence of interest and with said probe, said reagent being soluble in aqueous media and said at least one polymer molecule including at least two said oligonucleotide units per said polymer molecule.

2. A kit according to claim 1, wherein said oligonucleotide unit contains different hybridizing sequences that do not overlap for hybridizing with said sequence of interest and for hybridizing with said probe.

3. A kit according to claim 1, wherein said oligonucleotide unit contains different hybridizing sequences that do overlap for hybridizing with said sequence of interest and for hybridizing with said probe.

4. A kit according to claim 1, wherein said reagent contains from about 3 to 100 of the oligonucleotide units, per said polymer molecule.

5. A kit according to claim 1, wherein said at least one polymer molecule is formed by polymerization of unsaturated monomers.

6. A kit according to claim 1, wherein a precursor of said at least one monomeric unit carries a reactive function which is capable of reacting, either directly or by way of a bifunctional coupling agent, with a precursor of the oligonucleotide unit in order to form said lateral substituent.

7. A kit according to claim 3, wherein said sequence of interest and said probe competitively hybridize with a hybridizing sequence included in said oligonucleotide unit.

8. A kit according to claim 3, wherein said sequence of interest and said probe competitively and coextensively hybridize with a hybridizing sequence included in said oligonucleotide unit and said reagent includes at least three of said oligonucleotide units per said polymer molecule.

9. A kit according to claim 6, wherein said reactive function is selected from the group consisting of amine, imide, aldehyde, epoxy, thiol, halogenoalkyl and carboxylic acid functions, with the carboxylic acid function being selected from the group consisting of carboxylic acid and carboxylic acid activated in at least one form selected from the group consisting of acid halide form, anhydride form and ester form.

10. A kit according to claim 5, wherein said unsaturated monomers comprise a monomer selected from the group consisting of N-vinylpyrrolidone, methyl vinyl ether, ethylene, propylene and styrene.

11. A kit according to claim 1, wherein said oligonucleotide units are identical.

12. A kit for detecting at least one nucleic acid sequence of interest, with signal amplification, said kit having in suitable containers:
    a reagent; and
    a single species of tracer-labelled oligonucleotide probe reactive with said reagent;
    wherein said reagent comprises at least one linear backbone copolymer molecule having a backbone chain formed by carbon-to-carbon covalent bonds, said at least one copolymer molecule comprising a first type of monomeric unit and a second type of monomeric unit, wherein at least one of said first type of monomeric unit carries a lateral substituent, said lateral substituent comprising an oligonucleotide unit that hybridizes with said sequence of interest and with said probe, said reagent being soluble in aqueous media and said at least one copolymer molecule including at least two said oligonucleotide units per said copolymer molecule.

13. A kit according to claim 12, wherein said copolymer molecule is formed by polymerization of a first unsaturated monomer and a second unsaturated monomer.

14. A kit according to claim 12, wherein said at least one lateral substituent is not present on said second type of monomeric unit.

15. A kit according to claim 12, wherein said oligonucleotide unit contains different hybridizing sequences that do not overlap for hybridizing with said sequence of interest and for hybridizing with said probe.

16. A kit according to claim 12, wherein said oligonucleotide unit contains different hybridizing sequences that do overlap for hybridizing with said sequence of interest and for hybridizing with said probe.

17. A kit according to claim 16, wherein said sequence of interest and said probe competitively hybridize with a hybridizing sequence included in said oligonucleotide unit.

18. A kit according to claim 16, wherein said sequence of interest and said probe competitively and coextensively hybridize with a hybridizing sequence included in said oligonucleotide unit and said at least one copolymer molecule includes at least three of said oligonucleotide units per said copolymer molecule.

19. A kit according to claim 12, wherein said at least one copolymer molecule contains from 3 to 100 of the oligonucleotide units per said copolymer molecule.

20. A kit according to claim 12, wherein said at least one copolymer molecule is a bipolymer.

21. A kit according to claim 13, wherein said first monomer carries a reactive function which is capable of reacting, either directly or by way of a bifunctional coupling agent, with a precursor of the oligonucleotide unit in order to form said lateral substituent.

22. A kit according to claim 21, wherein said reactive function is selected from the group consisting of amine, imide, aldehyde, epoxy, thiol, halogenoalkyl and carboxylic acid functions, with the carboxylic acid function being selected from the group consisting of carboxylic acid and carboxylic acid activated in at least one form selected from the group consisting of acid halide form, anhydride form and ester form.

23. A kit according to claim 21, wherein said first monomer is a derivative of an unsaturated carboxylic acid.

24. A kit according to claims 23, wherein said acid is selected from the group consisting of acrylic, methacrylic and maleic acids.

25. A kit according to claim 23, wherein said derivative is selected from the group consisting of anhydrides, acid halides and esters.

26. A kit according to claim 23, wherein said second monomer is selected form the group consisting of N-vinylpyrrolidone, methyl vinyl ether, ethylene, propylene and styrene.

27. A kit according to claim 12, wherein said oligonucleotide units are identical.

* * * * *